United States Patent [19]
Tackett et al.

[11] Patent Number: 5,691,809
[45] Date of Patent: Nov. 25, 1997

[54] METHOD AND APPARATUS FOR STUDYING ORGANIC DEPOSITION

[75] Inventors: James E. Tackett, Castlerock; Gary R. Cook, Highlands Ranch; Michael A. Jessee, Louviers, all of Colo.

[73] Assignee: Marathon Oil Company, Findlay, Ohio

[21] Appl. No.: 524,190

[22] Filed: Sep. 6, 1995

[51] Int. Cl.⁶ .................... G01N 21/64; G01N 33/26
[52] U.S. Cl. ................................................ 356/72
[58] Field of Search .................................. 356/72

[56] References Cited

U.S. PATENT DOCUMENTS

| | | | |
|---|---|---|---|
| 3,375,802 | 4/1968 | Lazarre | 116/117 |
| 3,829,761 | 8/1974 | Shimizu et al. | 324/30 B |
| 4,425,810 | 1/1984 | Simon et al. | 73/863.11 |
| 4,715,711 | 12/1987 | Dunn | 356/246 |
| 5,046,854 | 9/1991 | Weller et al. | 356/440 |

OTHER PUBLICATIONS

Thomas et al., "Experimental and theoretical studies of solids precipitation from reservoir fluid," *The Journal of Canadian Petroleum Technology*, V. 1.31, No. 1 (1991), pp. 22–33.

Fotland, et al., "Detection of Asphaltene Precipitation and Amounts Precipitated by Measurement of Electrical Conductivity," *Fluid Phase Equilibria*, vol. 82, (1993), pp. 157–164.

Downare et al., "Visible and Near–Infrared Fluorescence of Curde Oils," *Applied Spectroscopy*, vol. 49, No. 6 (1995), pp. 754–764.

Zhu et al., "Temperature Dependence of Fluorescence of Crude Oils and Related Compounds," *Energy and Fuels*, vol. 6, No. 5 (1992) pp. 545–552.

MacMillan et al., "A Unified Approach to Asphaltene Precipitation: Laboratory Measurement and Modeling," *SPE 28990*, Feb. 1995., pp. 471–480.

*Primary Examiner*—Vincent P. McGraw
*Attorney, Agent, or Firm*—Jack L. Hummel; Jack E. Ebel

[57] ABSTRACT

A method and apparatus for studying the conditions under which multiple condensed phases form during production, transportation, and processing of crude oil and other organic liquids. The sample temperature and pressure are controlled, and changes in fluorescence and/or electrical conductance or conductivity occurring within the sample due to formation of multiple condensed phases are detected. The measurements are made using a cell containing the liquid sample at elevated temperature and pressure. The cell has a generally cylindrical housing and separate means for visually inspecting a liquid sample which is present within the cell, controlling the temperature of the liquid sample, controlling the pressure of the liquid sample, detecting fluorescence changes occurring within the sample, and determining the electrical conductivity of the sample.

28 Claims, 6 Drawing Sheets

METHOD AND APPARATUS FOR STUDYING ORGANIC DEPOSITION

BACKGROUND OF THE INVENTION

1. Field of the Invention

The present invention relates to a method and apparatus for determining the temperature, pressure, and/or composition ranges at which organic deposition occurs within a liquid, and more particularly, to a method and apparatus whereby data from electrical conductance measurements, visual observation, and fluorescence detection are utilized to determine such temperature, pressure, and/or composition ranges.

2. Description of Related Art

The deposition of organic compounds, for example asphaltene and/or wax, in a subterranean hydrocarbon bearing formation, in a wellbore penetrating such a formation, or in equipment associated with the transportation or processing of hydrocarbons produced from such a formation can cause severe production problem, such as in situ permeability reductions and plugging of wellbore or transportation tubulars, respectively. In an attempt to define and thus avoid the temperature, pressure, and composition conditions which favor such organic deposition and thereby minimize such production problems, a sample of produced hydrocarbons has been placed within a controlled environment, such as a cell. The temperature and pressure of the cell and the composition of the hydrocarbon sample may then be varied and/or chemical additives may be incorporated into the hydrocarbon sample to simulate potential production conditions. Thereafter, the controlled environment is observed to detect the presence of any organic deposits. In this manner, temperature and pressure ranges in which organic deposition occurs can be defined and incorporated into methods for inhibiting such deposition.

A high temperature, high pressure cell has been employed in conjunction with spectroscopic detection apparatus to determine such temperature and pressure ranges. Specifically, a near infrared laser system has been used to measure energy transmission through a hydrocarbon sample. The use of transmission spectroscopy in this application requires the use of very small optical path lengths on the order of 1 mm to 8 mm for measuring dark samples, such as crude oil. In order to meet such a requirement, a sample is usually pumped from a conditioning cell where the conditions, such as temperature, pressure, and sample composition, are varied to a separate detection cell via a line. Such an assembly was described by F. B. Thomas et al., in "Experimental and theoretical studies of solids precipitation form reservoir fluid", *The Journal of Canadian Petroleum Technology* Vol. 31, No. 1 (1991), pp. 22–30. Using this assembly, organic material may deposit in the line between the conditioning and detection cells, and therefore, plug this line and/or be difficult to detect in the detection cell. Further, since a near infrared laser system only emits one useful wavelength of light, this system only can detect a decrease in energy transmission. Thus, the exact cause of such an energy decrease cannot be determined without conducting additional tests. A similar system is described in U.S. Pat. No. 4,425,810 issued on Jan. 17, 1984 to Simon et al. in which the cell is constructed of sapphire and is provided with a transparent window which permits optical access into and out of the cell and can be used to transmit gamma rays to determine material density. A probe within the cell functions to collect a subsample for movement to a separate apparatus for measuring properties.

P. Fotland et al. describe a method for detecting asphaltene precipitation based on measurements of electrical conductivity in "Detection of Asphaltene Precipitation and Amounts Precipitated by Measurement of Electrical Conductivity," *Fluid Phase Equilibria* Vol. 82 (1993), pp. 157–164. Fotland et al. used a low conductivity cell comprising two concentric cylinders and electrodes which have been electrolytically plated with gold. An empirically determined functional relationship between conductivity and asphaltene precipitation was validated by gravimetric measurements and optical microscopy. The measurements were made at ambient temperature and pressure.

In view of this, a need exists for an apparatus and method to completely and accurately determine temperature, pressure, and/or composition ranges in which organic deposition occurs in a given liquid hydrocarbon sample.

Accordingly, it is an object of the present invention to provide a method for accurately determining the temperature, pressure, and/or composition ranges at which organic deposition from a liquid occurs.

It is a another object of the present invention to provide a method utilizing multiple types of data concerning a liquid sample so that a more accurate determination of temperature, pressure, and/or composition ranges at which organic deposition occurs within the liquid can be made.

It is a further object of the present invention to provide a high temperature, high pressure cell for accurately determining the temperature, pressure, and/or composition ranges at which organic deposition from a liquid occurs.

It is a still further object of the present invention to provide a cell which collects multiple types of data concerning a liquid sample so that a more accurate determination of temperature and/or pressure ranges at which organic deposition occurs within the liquid can be made.

SUMMARY OF THE INVENTION

To achieve the foregoing and other objects, and in accordance with the purposes of the present invention, as embodied and broadly described herein, one characterization of the present invention is a method for determining conditions at which at least one condensed phase forms in an organic liquid sample. The sample temperature and pressure are controlled, and changes in one or more physical properties are detected which occur due to formation of one or more condensed phases in the liquid. The physical properties include fluorescence, electrical conductance, and conductivity. Simultaneous measurements of more than one property may be made. The pressure and temperature at which the at least one condensed phase forms are also determined. Fluorescence changes are detected by operating a fluorescence spectrometer in emission mode, excitation mode, synchronous mode, or a combination thereof.

Another characterization of the present invention is a cell for determining conditions at which organic deposition occurs from a liquid sample. The cell comprises a generally cylindrical housing having a sidewall and first and second opposing ends. A first cap is secured to the first end of the housing and a second cap is secured to the second end of the housing. Separate means are provided for visually inspecting a liquid sample which is present within the cell, for controlling the temperature of the liquid sample, for controlling the pressure of the liquid sample, for detecting fluorescence changes occurring within the sample, and for determining the electrical conductivity of the sample.

BRIEF DESCRIPTION OF THE DRAWINGS

The accompanying drawings, which are incorporated in and forms a part of the specification, illustrate the embodiments of the present invention and, together with the description, serve to explain the principles of the invention.

In the drawings.

DETAILED DESCRIPTION OF THE PREFERRED EMBODIMENTS

When some liquid hydrocarbon mixtures, such as crude oils, are subjected to certain temperature and pressure conditions, additional condensed phases form in the oil. The condensed phases may comprise asphaltenes and/or wax. Asphaltenes are believed to form a micellar system within the oil. Pressure, temperature, and compositional changes can break the micelles and cause asphaltene aggregation and precipitation. Paraffin or wax molecules are soluble in the oil at temperatures above the wax cloud point. When the oil is cooled below the wax cloud point, wax crystals form. The asphaltenes and/or wax crystals may aggregate, resulting in a droplet or particle size too large to remain suspended in the oil. One embodiment of the present invention comprises a method for determining the conditions under which one or more condensed phases form in liquid samples, such as oils. The method of the present invention utilizes a calibration procedure and an evaluation procedure. During the calibration procedure, measurements are made in an oil sample under known pressure and temperature conditions to establish the characteristics of the particular sample with and without a separate condensed phase, such as asphaltene or wax. The temperature, pressure, and composition can be individually varied to determine how the sample behavior changes in response to changes in each of these variables. Once the nature of these variations is known, the behavior of the oil at a given combination of temperature, pressure, and composition can be predicted. The behavior of the oil in the presence of asphaltene and/or wax can also be predicted. The presence or absence of the asphaltene and/or wax phase should be verified by an appropriate method known to those skilled in the art, such as by visual observation, differential scanning calorimetry, or filtering the liquid and inspecting the filtrate.

During the evaluation procedure, the liquid sample is placed in a cell and subjected to pressure, temperature, and composition conditions simulating those anticipated or found in hydrocarbon reservoirs, wells, and pipelines, and additional measurements are made to determine the behavior of the sample under those conditions. The observed behavior of the oil sample is compared with the predicted behavior of the liquid with and without a separate asphaltene or wax phase present, based on the results of the calibration procedure. If the observed behavior of the sample departs from the expected behavior in a manner which is consistent with the expected behavior of the sample in the presence of asphaltene and/or wax, the presence of the additional phase is indicated. The method of the present invention utilizes fluorescence spectrometry measurements and/or electrical measurements and, optionally, visual observations. As used herein, "electrical measurements" refers to measurements of the electrical conductance or conductivity of a sample.

Fluorescence is a phenomenon, exhibited by some chemical compounds, in which light is absorbed at one wavelength by a molecule and emitted at a second, usually longer, wavelength. Fluorescence has been observed in oil samples at wavelengths ranging from near infrared to near ultraviolet. The energy differences between the excitation and emission wavelengths result from excitation and decay of electrons to different energy levels. The fluorescence of a sample of a compound or mixture of compounds may be observed with a fluorescence spectrometer having an excitation diffraction grating or prism for varying the wavelength of the light reaching the sample and an emission diffraction grating or prism for varying the wavelength of the light emitted by the sample and reaching a detector. The spectrometer may be run in the excitation mode, where the excitation grating or prism is moved and the emission grating or prism remains fixed, thereby scanning the excitation spectrum. In the emission mode, the excitation grating or prism remains fixed and the emission grating or prism is moved, thereby scanning the emission spectrum. Both gratings or prisms are moved in the synchronous scanning mode. In the following discussion, the terms "fluorescent" and "fluorescence" may refer to the phenomenon detected by the spectrometer in any of these three modes. Fluorescence measurements can be obtained for materials too opaque for other optical measurements.

Aromatic compounds present in both the asphaltene and non-asphaltene portions of crude oil fluoresce, with a fluorescence spectrum which depends upon the composition of the oil. Thus, each crude oil and asphaltene portion exhibits a characteristic "signature" spectrum. Paraffin waxes do not fluoresce, although they may contain entrained fluorescent material.

The shape and intensity of the signature spectrum of an oil sample are strongly affected by dilution of the oil with a solvent, such as benzene or a light alkane. These effects have been attributed to quenching during molecular collisions in a paper by T. D. Downare and O. C. Mullins, entitled "Visible and Near-Infrared Fluorescence of Crude Oils," which appeared in *Applied Spectroscopy*, Vol 49, No. 6 (1995) pp. 754–764, and which is incorporated herein by reference. Signature spectra also vary with pressure and with temperature, as described in a paper by Y. Zhu and O. C. Mullins, entitled "Temperature Dependence of Fluorescence of Crude Oils and Related Compounds," which appeared in *Energy and Fuels*, Vol. 6, No. 5, (1992) pp. 545–552, and is also incorporated herein by reference.

Light scattering off particles suspended within an oil sample also affects the fluorescence spectrum of the sample in a wavelength-dependent manner. Therefore, an oil sample has a different signature spectrum when asphaltene and/or wax droplets or particles are present. In addition to scattering light, asphaltene particles have different fluorescence spectra from micellar asphaltenes. Thus, the signature spectrum of an oil containing asphaltene droplets is also influenced by the decrease in micellar asphaltenes and the fluorescence of the asphaltene droplets or particles.

In one calibration procedure in accordance with the method of the present invention, the signature spectrum of an oil sample is obtained at a predetermined temperature, pressure, and composition. The temperature, pressure, and composition can be individually varied to determine how the spectrum changes in response to changes in each of these variables. Once the nature of these variations is known, the spectrum of the oil at a given combination of temperature, pressure, and composition can be predicted and compared with spectral data obtained during the evaluation procedure.

Several factors other than the characteristics of the oil can also influence oil spectra. For example, variations in the intensity of the light source, the detector efficiency, the sample container, or the sample position relative to the source or detector may change the measured intensity of a spectrum. However, these additional factors generally influence an entire spectrum in the same manner and pose potential interpretation difficulties only in comparisons of measurements made at different times. By looking at the ratio of the signal intensities from a single spectrum at two wavelengths, the effects of signal and detector variations and sample positioning can be minimized, leading to more accurate comparisons and interpretations of data obtained at different times. As is apparent to one skilled in the art, the signature spectra should be obtained with the same sample/detector geometry that will be used for subsequent observations of asphaltene and/or wax formation and/or deposition.

The signature spectra of an oil sample with dissolved paraffins and/or asphaltenes and the same sample with separate asphaltene and/or wax phases can be compared to determine two or more optimum wavelengths to use in the signal ratios. Ideally, the wavelengths will be selected so that the signal ratios are significantly different for the two signature spectra, thereby facilitating the detection of the asphaltene and/or wax phase. Using more than two excitation wavelengths may aid in distinguishing asphaltene from wax phases.

Signature spectra can be determined with a fluorescence spectrometer, such as a Perkin Elmer model LS 50B, for a particular type of oil containing an asphaltene and/or wax fraction. The spectrometer can be run in any mode to obtain a signature spectrum. In particular, scattering can easily be observed in any of the three fluorescence modes. The spectrometer can also be run in any mode for subsequent evaluations utilizing the data in the signature spectrum.

Wax formation in oil samples can be studied in any fluorescence mode. Light scattering is the primary factor affecting fluorescence when wax crystals form, and scattering causes the fluorescence intensities of oil samples containing paraffins to vary uniformly with temperature but change abruptly when light scattering occurs due to wax crystallization. The effects of scattering are easily detectable in each of the three fluorescence spectrometry modes. In the calibration procedure, the signature fluorescence spectra for an oil sample containing dissolved wax and for the same oil containing wax crystals are determined at a series of temperatures above and below the suspected wax cloud point temperature. Wax cloud point temperatures are generally less than 170° F. Preferably, the presence of wax, father than another material such as asphaltenes, should be confirmed by another technique, such as differential scanning calorimetry. Two or more wavelengths are selected from the signature spectra for use in signal ratios for detecting the presence of a wax phase. Although the wax cloud point is composition, pressure, and temperature dependent, the known effects of composition and pressure on the signature spectra can be used to predict the signal ratios at other pressures. Thus, the signal ratios based on the signatures can be established using dead oil at atmospheric pressure during the calibration procedure and then applied to live or recombined oil samples at reservoir conditions in the evaluation procedure.

In accordance with the present invention, a more complex calibration procedure may be utilized for studying asphaltene deposition. It is generally preferred that the asphaltene evaluation procedure is based excitation signature spectra. However, one or more emission spectra are first obtained for the oil sample with and without an asphaltene phase to determine one or more optimum emission wavelengths at which to obtain the calibration and evaluation excitation data. Addition of a sufficient quantity of a non-fluorescent organic diluent, such as a light alkane, causes an asphaltene phase to separate from the oil. Pentane and n-hexane are preferred as diluents. Thus, by incrementally adding portions of the diluent and determining the excitation spectrum after each addition, the signature emission and excitation spectra of the crude oil containing dissolved asphaltene or a combination of wax and asphaltene can be distinguished from the signature emission and excitation spectra of the oil with a separate asphaltene phase present. If the fluorescence signals are detected through a window at the bottom of the sample container or cell, an additional signature spectrum results from increased scattering when asphaltenes deposit on the window. The signature spectra of an oil and its asphaltene fraction can be obtained with a dead oil sample at ambient pressure and, and the known effects of the volatile components and increased pressure can be utilized to predict the spectrum of a live or recombined oil at reservoir pressure.

One or more emission wavelengths are then be selected for subsequent excitation measurements. Excitation spectra are obtained for the oil and the asphaltene wax portion with the emission grating set at each selected emission wavelength. If more than one emission wavelength is selected, separate excitation measurements are made for each emission wavelength.

The signal ratios of the single-phase and two-phase systems are generally different, smoothly varying functions of temperature and pressure. In accordance with the evaluation procedure of the present invention, a sample is subjected to temperature, pressure, and composition conditions approximating the conditions anticipated in a subterranean formation, well, or pipeline, and the conditions are systematically varied through a range of temperatures, pressures, and/or compositions of interest. Fluorescence spectra are obtained at each temperature, and signal ratios are then determined for each spectrum. The signal ratios vary smoothly as the conditions change until one or more new condensed phases form in the liquid. Formation of a new phase causes an abrupt change in the signal ratio.

Electrical measurements are also used in accordance with the method of the present invention to determine the conditions under which one or more condensed phases form. The electrical conductance or conductivity of a crude oil sample depends upon the concentration and mobility of charged components of the sample. Charged components may include organic molecules with functional groups capable of ionization in an electric field. Examples of such compounds include amines and carboxylic acids. Mixing the oil sample with another substance can affect the oil conductance. Viscosity changes due to the presence of an additive can alter the ion mobility and, therefore, the oil conductance. Additional changes in conductance arise from the conductance properties of the additive. Aromatic compounds, such as asphaltenes, dissolved in the oil also contribute to the oil conductance due to the aromatic πelectrons. Thus, different oils exhibit different conductance behaviors, and the conductance data from each sample must be examined using the calibration procedure to determine the conductance changes which result from the onset of an asphaltene phase. Paraffins, from which waxes form, do not affect the oil conductance. Thus, conductance changes are observed when the asphaltenes separate from the oil, but not when waxes crystallize. If the conductance electrodes are not located at the bottom of the cell, there is no effect on the conductance due to asphaltene droplets or wax crystals falling from suspension. As is apparent to one skilled in the art, the sample conductivity and the electrode geometry determine the measured conductance, and, therefore, conductivity may also be determined for a given electrode geometry.

Optionally, fluorescence and electrical measurements may be combined with each other and/or with visual observations to determine whether material has been deposited within the cell, particularly on the cell window. Due to the opacity of most oils, visual observations made are most easily when a vapor phase is present.

After the calibration data are obtained for an oil sample, a series of measurements and/or visual observations can then be made under varying temperature and/or pressure conditions to determine the behavior of the asphaltene and/or wax components of the oil. For example, the sample can be heated above the wax cloud point and/or asphaltene formation temperature and then cooled at a controlled rate to determine the temperatures at which asphaltene or wax formation begins and at which droplets and/or particles fall out of suspension in the oil. It is preferred that the sample be cooled slowly, at a rate less than 2° F. per minute, to prevent supercooling of the liquid. Use of a programmable cooling device facilitates slow, controlled cooling of the sample.

The sample pressure can be varied, either independently of temperature or simultaneously with temperature, and the conditions determined for the onset of formation of an asphaltene or wax phase and for the formation of asphaltene and/or wax deposits. The composition of the oil can also be varied to determine whether asphaltene and/or wax phase separation will occur under expected temperature and pressure conditions. For example, a proposed lift gas, asphaltene solvent, wax solvent, or other additive may be combined with the oil to determine the compatibility of the additive and the oil with respect to separation of asphaltenes and/or wax from the oil. It is preferred that the additive be a miscible gas or liquid; particles, immiscible liquid droplets, and gas bubbles cause increased light scattering and complicate the fluorescence measurements. However, it is necessary to find out how the fluorescence spectrum and the electrical properties of the oil and dissolved asphaltenes and/or wax change as a function of temperature, pressure, and composition in the absence of asphaltene and/or wax deposition in order to interpret the results correctly. Parameters derived from fluorescence and/or conductance data may be utilized in an appropriate thermodynamic model to predict the behavior of an oil under different conditions.

One advantage of the method of the present invention is that the light does not have to pass entirely through the sample to reach the detector. The ultraviolet and/or visible light must pass through a sufficient portion of the sample to cause detectable optical fluorescence and/or scattering. For uniform results, the sample should be thicker than the distance the light can travel through the sample. Another advantage of the method of the present invention is that spectral data, rather than just single wavelength data, are obtained, which allows the fluorescence pattern to be used to characterize the changes that occur. Combining data from electrical conductance measurements, fluorescence detection, and visual observation significantly enhances the ability to interpret experimental results.

Figure 1:
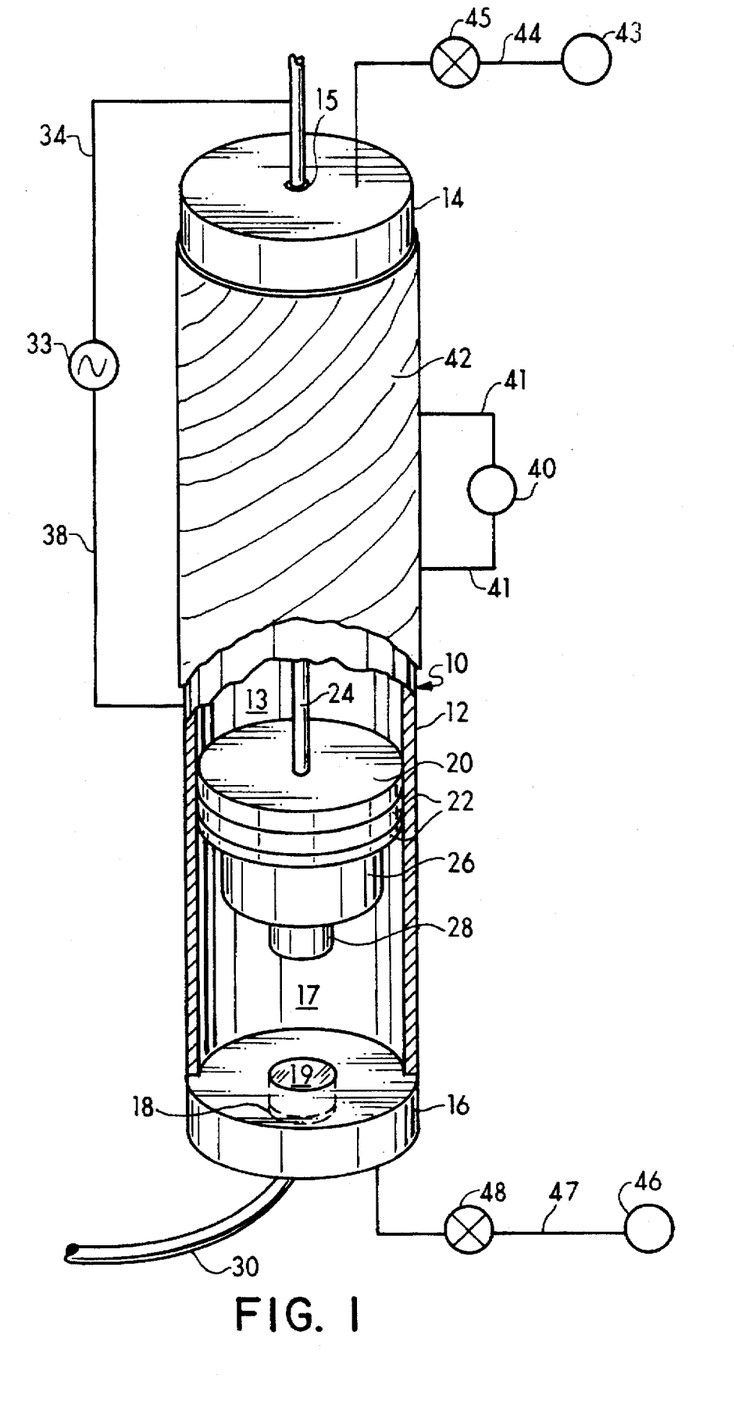
FIG. 1 is a partially cutaway perspective view of one embodiment of the organic deposition cell of the present invention.

Another embodiment of the present invention is a cell, illustrated generally as 10 in FIG. 1, having an elongated, generally tubular configuration defining a sidewall 12. Cell 10 has end caps 14 and 16 secured to separate ends of the cell by any suitable means, such as by screws inserted into threaded holes in the end caps (not illustrated). End cap 14 is provided with an aperture 15 therethrough. End cap 16 is provided with a void 19 which preferably has a generally cylindrical configuration. A transparent window 18 is secured to end cap 16 and is aligned with void 19 to permit visual inspection of a liquid sample present within cell 10 and the use of a fiber optic probe as hereinafter detailed for fluorescence detection of organic deposition or other changes that might occur. Preferably, window 18 is constructed of sapphire and is approximately ½ inch in thickness.

A piston 20 which constructed of any suitable material, for example plastic, is slidably positioned within cell 10 and is secured to a rod like shaft 24 which extends through aperture 15 in end cap 14. A plurality of O-ring seals 22 are positioned about piston 20 to provide a fluid tight seal between sidewall 12 of cell 10 and piston 20, thereby defining first and second volumes 13 and 17, respectively, within cell 10. A first conductance electrode 26 is secured to the face of piston 20 which bounds second volume 17 and is preferably constructed of stainless steel. At least the inside surface of sidewall 12 is formed from an electrically conductive material and functions as a second electrode. A protuberance 28 may be integrally formed with or is secured to the free face of first electrode 26 and is sized to be received within void 19 in end cap 16 so as to eliminate dead volume within cell 10 prior to a liquid sample being introduced therein. Elimination of the dead volume is important to prevent expansion of the liquid sample into a two phase system, thereby reducing the possibility of asphaltene and/or wax precipitation prior to measurement. A fiber optic probe 30 is positioned adjacent window 18 and secured to end cap 16 for fluorescence detection. End cap 14 is provided with a flow line 44 having a valve 45 to permit the controlled introduction and withdrawal of hydraulic fluid into first volume 13 in cell 10. The hydraulic fluid may be any hydraulic fluid suitable for use at the temperatures and pressures involved, such as a silicate ester fluid manufactured under the trade name MV-2 by Chevron Chemical Company. Pump 43 is utilized to control the pressure of hydraulic fluid which is introduced into volume 13. End cap 16 is connected to pump 46 by a flow line 47 having a valve 48 to permit the controlled introduction and withdrawal of a liquid sample, for example crude oil, into second volume 17 in cell 10, and to a pressure indicator (not shown) to measure pressure in second volume 17 to aid in filling and maintaining pressure in second volume 17.

A temperature controller 40 is electrically connected by means of wires 41 to a heating element 42 which is adjacent sidewall 12. Element 42 is preferably positioned around substantially the entire periphery and along substantially the entire length of cell 10. A cooling means, not shown, may also be provided and electrically connected to temperature controller 40. Preferably, temperature controller 40 is programmable to facilitate controlled temperature changes. A vector impedance analyzer 33 is secured to shaft 24 by means of electrical wire 34 and sidewall 12 of cell 10 by means of electrical wire 38. Shaft 24 is in electrical contact with first conductance electrode 26 but electrically isolated from end cap 14 by any suitable means, such as an O ring (not illustrated) mounted in aperture 15.

Cell 10 is constructed to withstand pressures on the order of 6000 psia and temperatures approximating 250° F. In operation, a liquid sample is introduced into volume 17 of cell 10 via line 47 and valve 48. Hydraulic fluid is introduced into volume 13 of cell 10 by means of line 44 and valve 45. Prior to introduction of a liquid sample into volume 17, protuberance 28 is immediately adjacent to window 18, thereby minimizing the magnitude of the dead volume within volume 19. It is preferred that the liquid within volume 17 is well mixed. Thus, cell 10 may be rocked during use, or a circulating pump may be utilized to enhance mixing. A filter may be placed in the circulation line between the cell and the pump to aid in detection of an asphaltene or wax phase. The electrical conductance of the liquid sample between sidewall 12 and first conductance electrode 26 is used to detect the onset of asphaltene deposition, two phase behavior and other changes that might occur within the sample. Alternatively, the measurement may be stated in terms of the electrical conductivity of the sample.

Window 18 is also used to detect the onset or presence of asphaltene deposition within the liquid sample by fluorescence. Fiber optic probe 30 comprises two fiber optic bundles, one for transmission of light to the sample and the other for transmission of light from the sample, and can be used to simultaneously transmit light to and from the cell for fluorescence detection of organic deposition or other changes that might occur. Ultraviolet and/or visible light is passed through the fiber optic probe via window 18 into the sample within volume 17 in cell 10. Emitted and scattered light are transmitted via window 18 and fiber optic probe 30 to a fluorescence spectrometer, such as that commercially available under the trade name LS 50B from Perkin Elmer Corporation, outside cell 10. Spectra obtained with the spectrometer are analyzed as described above. Window 18 can also be used to visually inspect the sample upon removal of probe 30 to determine the phase behavior of the sample. If desired, cell 10 may be turned upside down to prevent accumulation of a denser phase, such as asphaltene, wax, or water on window 18.

Figure 2:
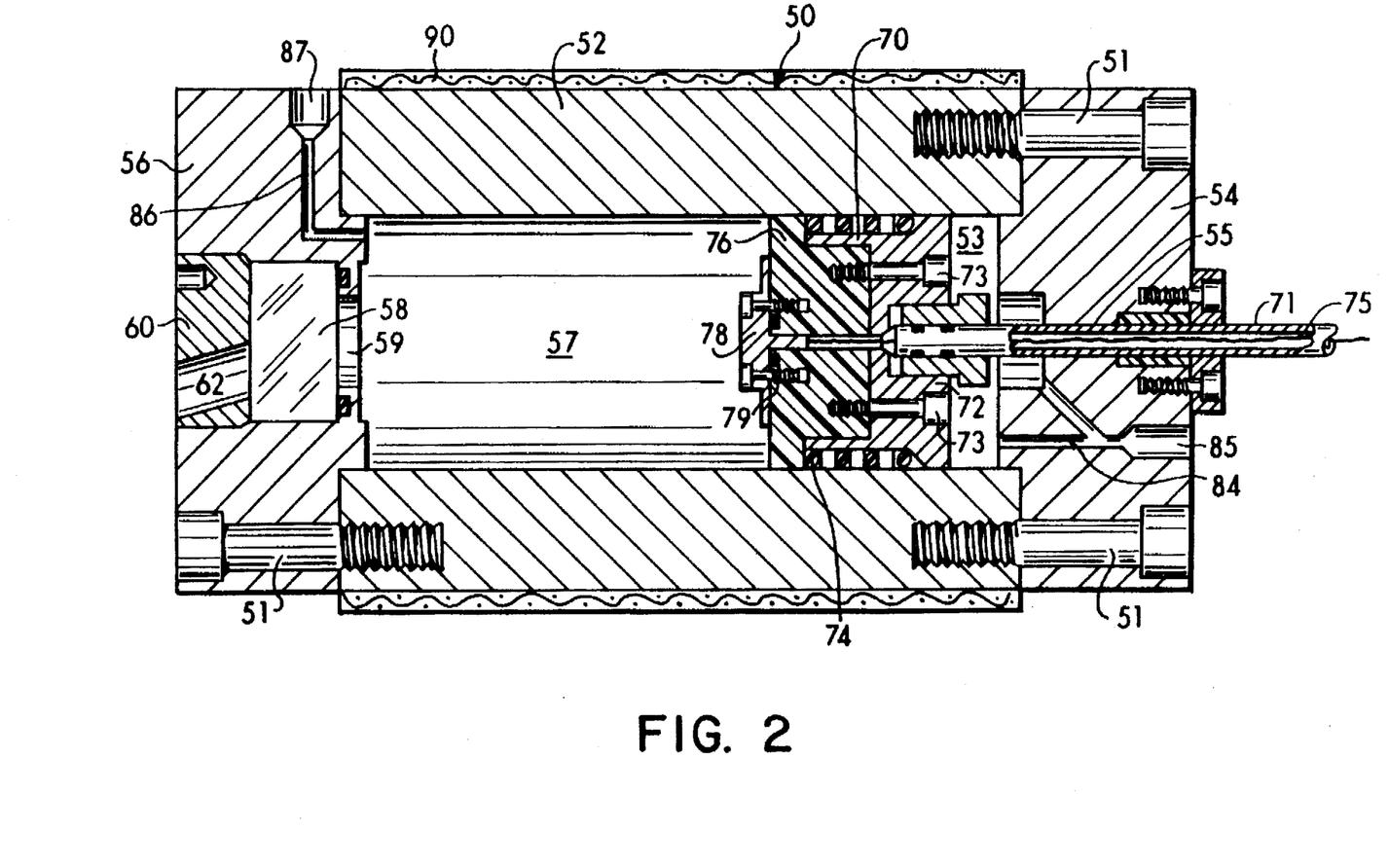
FIG. 2 is a cross sectional view depicting another embodiment of the organic deposition cell of the present invention.

A further embodiment of the cell of the present invention is illustrated generally as 50 in FIG. 2. Cell 50 has a generally tubular configuration defining a sidewall 52 having an electrically conductive inside surface. The inside surface functions as a second electrode. Cell 50 has end caps 54 and 56 secured to separate ends of the cell by any suitable means, such as bolts 51. End cap 54 is provided with an aperture 55 therethrough. End cap 56 is provided with a void 59 which preferably has a generally cylindrical configuration. A transparent window 58 is secured to end cap 56, for example by means of plug 60 which is secured to end cap 56 by screw threads. Window 58 is aligned with void 59 to permit visual inspection of a liquid sample present within cell 50 and the use of a fiber optic probe as previously detailed for fluorescence detection of organic deposition or other changes that might occur. Preferably, window 58 is constructed of sapphire and is approximately ¾ inch in thickness.

A piston, illustrated generally as 70 in FIG. 2, has a first portion 72 and a second portion 76. First portion 72 is constructed of any suitable electrically conductive material, for example stainless steel, is slidably positioned within cell 50, and is secured to a rod-like shaft 71 which extends through aperture 55 in end cap 54. Second portion 76 is secured to first portion 72 by any suitable means, for example by bolts 73, and is constructed of a plastic, such as polyetheretherketone. A plurality of O-ring seals 74 are positioned between first portion 72 and second portion 74 about the periphery of piston 70 so as to provide a fluid tight seal between the inner diameter of side wall 52 of cell 50 and piston 70 thereby defining first and second volumes 53 and 57, respectively, within cell 50. A protuberance 78 is secured to the free face of probe 70 by means of bolts 79 and is sized to be received within void 59 in end cap 56 so as to eliminate dead volume within cell 50 prior to a liquid sample being introduced therein. Protuberance 78 is constructed of an electrically conductive material, such as stainless steel and functions as a first conductance electrode. Shaft 71 is hollow and an electrical wire 75 is positioned through shaft 71 and piston 70 and is connected to protuberance 78. A fiber probe is received within aperture 62 in plug 60 and is positioned adjacent to window 58 for fluorescence detection. End cap 54 is provided with a flow line 84 having a valve 85 to permit the controlled introduction and withdrawal of hydraulic fluid, such as mineral oil or another suitable fluid under pressure, into first volume 53 in cell 50. End cap 56 is provided with a flow line 86 having a valve 85 to permit the controlled introduction and withdrawal of a liquid sample, for example crude oil, into second volume 57 in cell 50. Another flow line 88 and valve 87 permit introduction of hydraulic fluid into first volume 53. In this embodiment, cell 50 is wrapped with an electrical heater or blanket 90. Heater 90 and a temperature controller (not shown) are used to control the temperature of fluid therein. Optionally, a cooling device (not shown) may be utilized to improve temperature control. The operation of cell 50 is similar to that described above for cell 10.

The present invention can be utilized to study formation and deposition of condensed phases under any temperature and pressure conditions reasonably expected in a hydrocarbon reservoir and which can be handled by the materials and construction of the cell in which the measurements are made. Measurements have been made successfully at temperatures up to 254° F. and 10,000 psig.

The following examples demonstrate the practice and utility of the present invention, but are not to be construed as limiting the scope thereof.

EXAMPLE 1

Cell 10 of FIG. 1 is constructed with a 1.5-inch inner diameter and is 20 inches long. In use, piston 20 is moved to a position in contact with window 18, and volume 17 is evacuated. 40 ml of recombined oil is then introduced via flow line 47 and valve 48 by reducing the pressure in volume 13, causing piston 20 to move away from the window. The pressure in cell 10 is increased to 5000 psig, and the temperature is maintained at 80° F. while it is rocked for 4 hours. Rocking is discontinued, and conductance and fluorescence readings are obtained. While maintaining the temperature at 80° F. and the pressure at 5000 psig, pentane is added to the crude oil incrementally to sequentially increase the volume ratio of pentane in the oil between 0.25 and 2.0. After each addition of pentane, the cell is rocked overnight and conductance and fluorescence measurements are obtained. A Hewlett-Packard 4192A Impedance Analyzer is used to make the conductance measurements with an alternating current of 1 V and 5 kHz. The current passes through the oil only for the short time needed to make each measurement.

Figure 3:
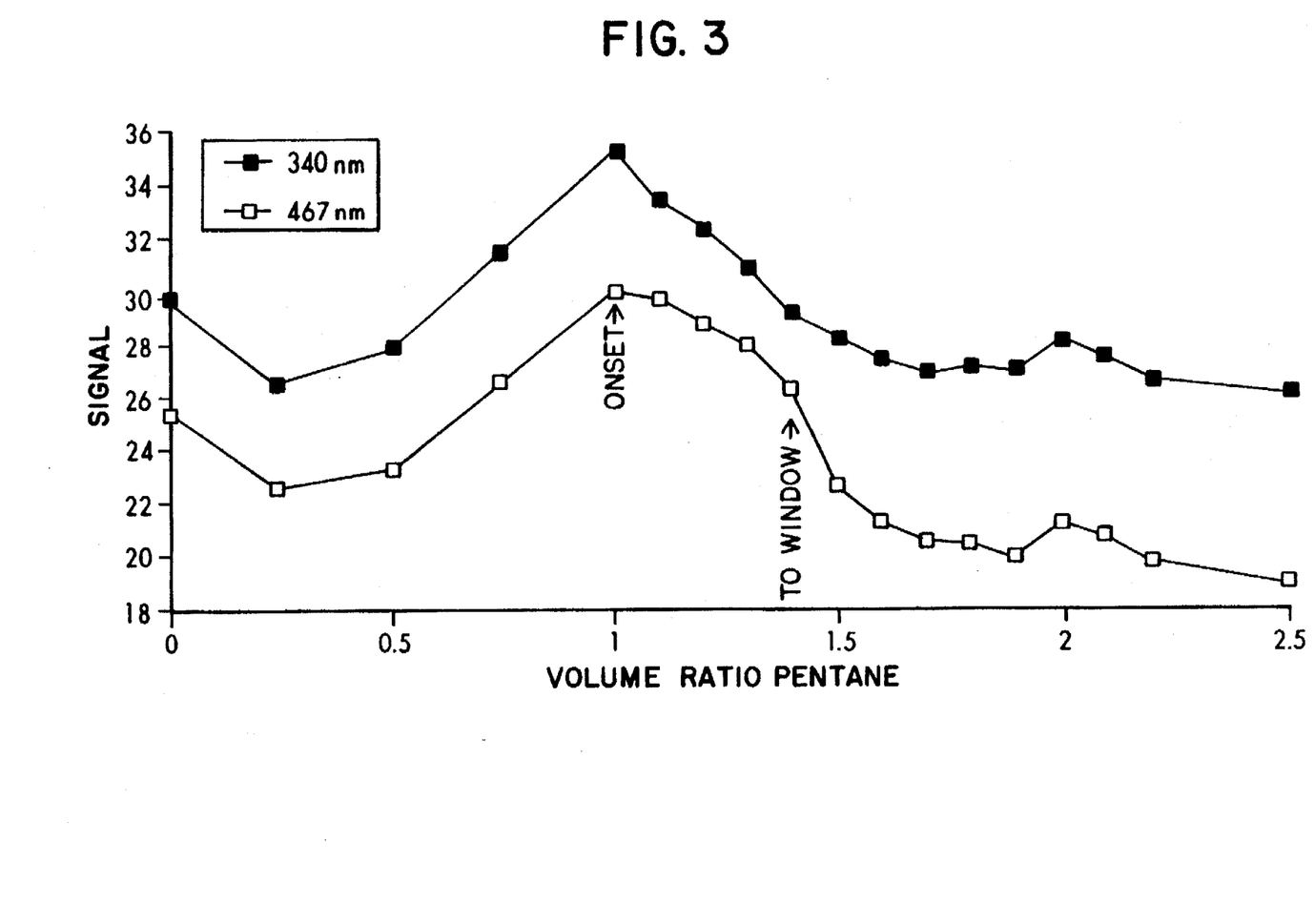
FIG. 3 is a graph showing the relative intensity of fluorescence signals at 340 nm and 467 nm obtained from an asphaltene-containing crude oil sample as a function of the volume ratio of pentane added to the sample.
Figure 4:
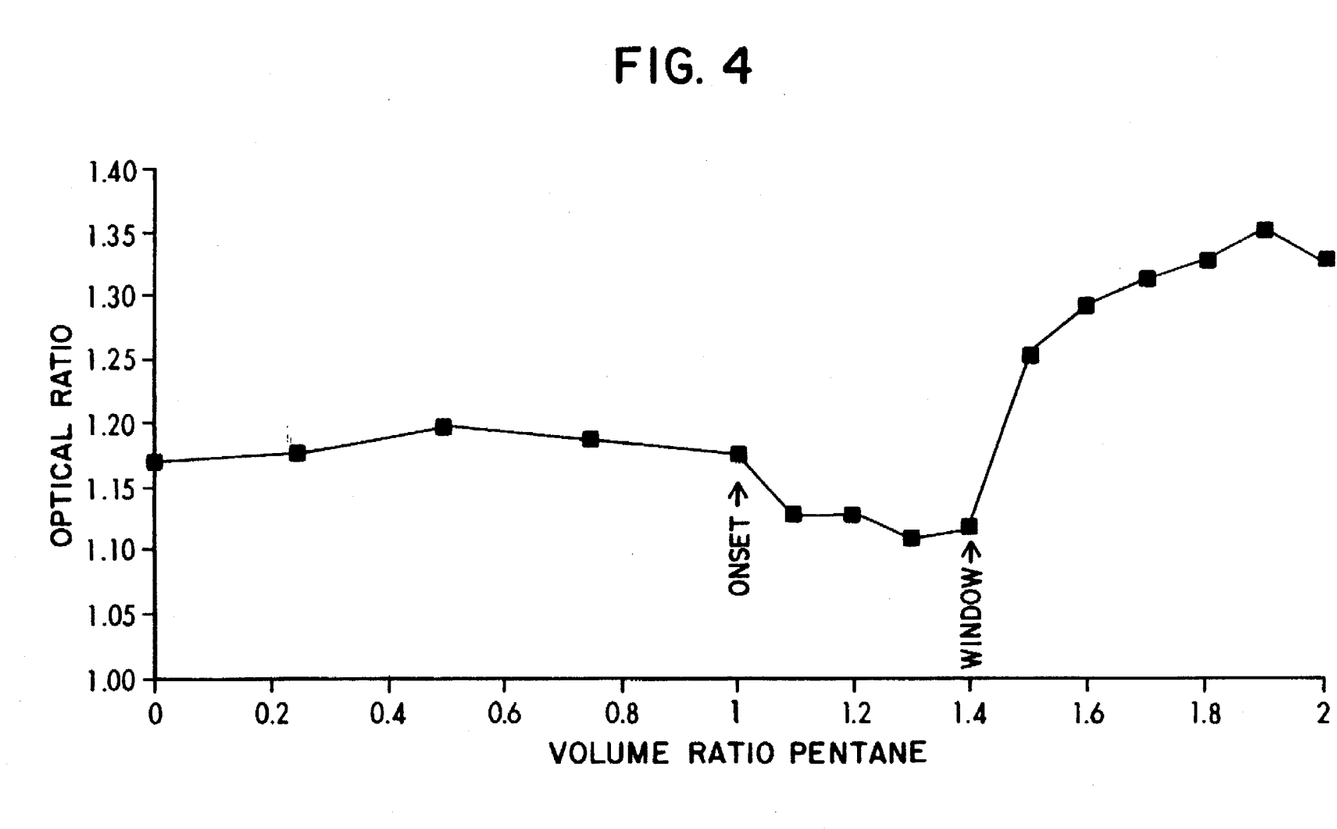
FIG. 4 is a graph showing the ratio of the fluorescence signal intensity at 340 nm to the signal intensity at 467 nm, obtained from the data shown in FIG. 3, as a function of the volume ratio of pentane added to the sample.

FIG. 3 compares the fluorescence signals obtained with the excitation grating set at 340 nm and 467 nm. Both signals increase at approximately the same rate as the volume ratio of pentane increases, up to a volume ratio of about 1, when asphaltene precipitation begins. The curves then decrease at different rates with increasing pentane volume ratios. The rate of decrease of the 467 nm signal increases abruptly at a pentane volume ratio of about 1.4, when asphaltene deposition on the cell window begins. FIG. 4 shows the optical ratio of the signal at 340 nm to the signal at 467 nm as a function of the pentane volume ratio. The optical ratio remains approximately constant until the onset of asphaltene precipitation, decreases to a second relatively constant value when asphaltene particles are present in the oil, and increases abruptly when asphaltene deposits form on the cell window.

Figure 5:
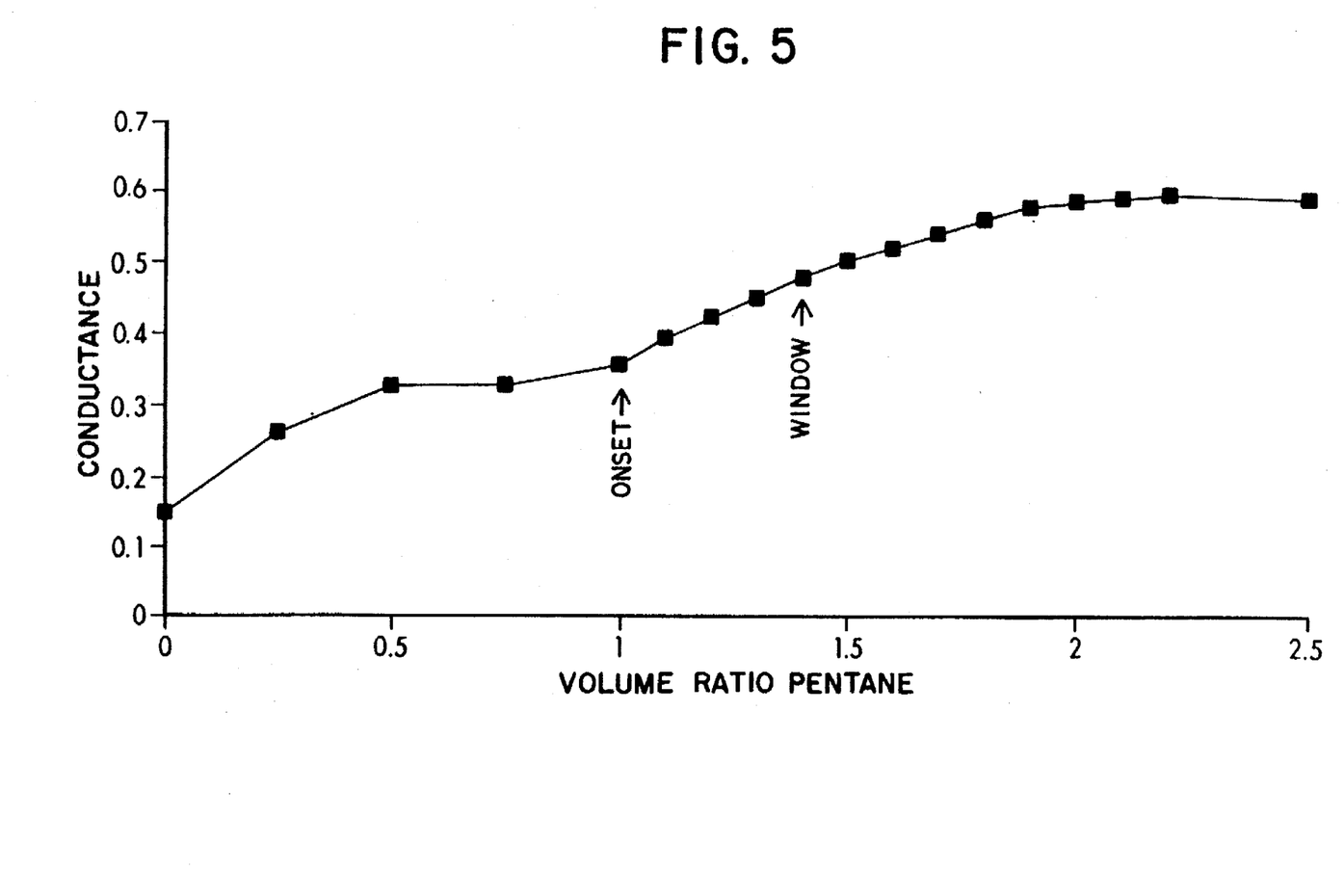
FIG. 5 is a graph showing the conductance of the crude oil sample of FIG. 3 as a function of the volume ratio of pentane added to the sample.

The conductances measured for the same sample are shown in FIG. 5. For pentane volume ratios between about 0.5 and 1.0, the conductance is approximately constant at about 3.2 mS. When the volume ratio is above 1, the conductance increases approximately linearly with the pentane volume ratio. Thus, the change in slope of the conductance curve indicates the onset of asphaltene precipitation. There is no effect due to asphaltene deposition.

EXAMPLE 2

Figure 6:
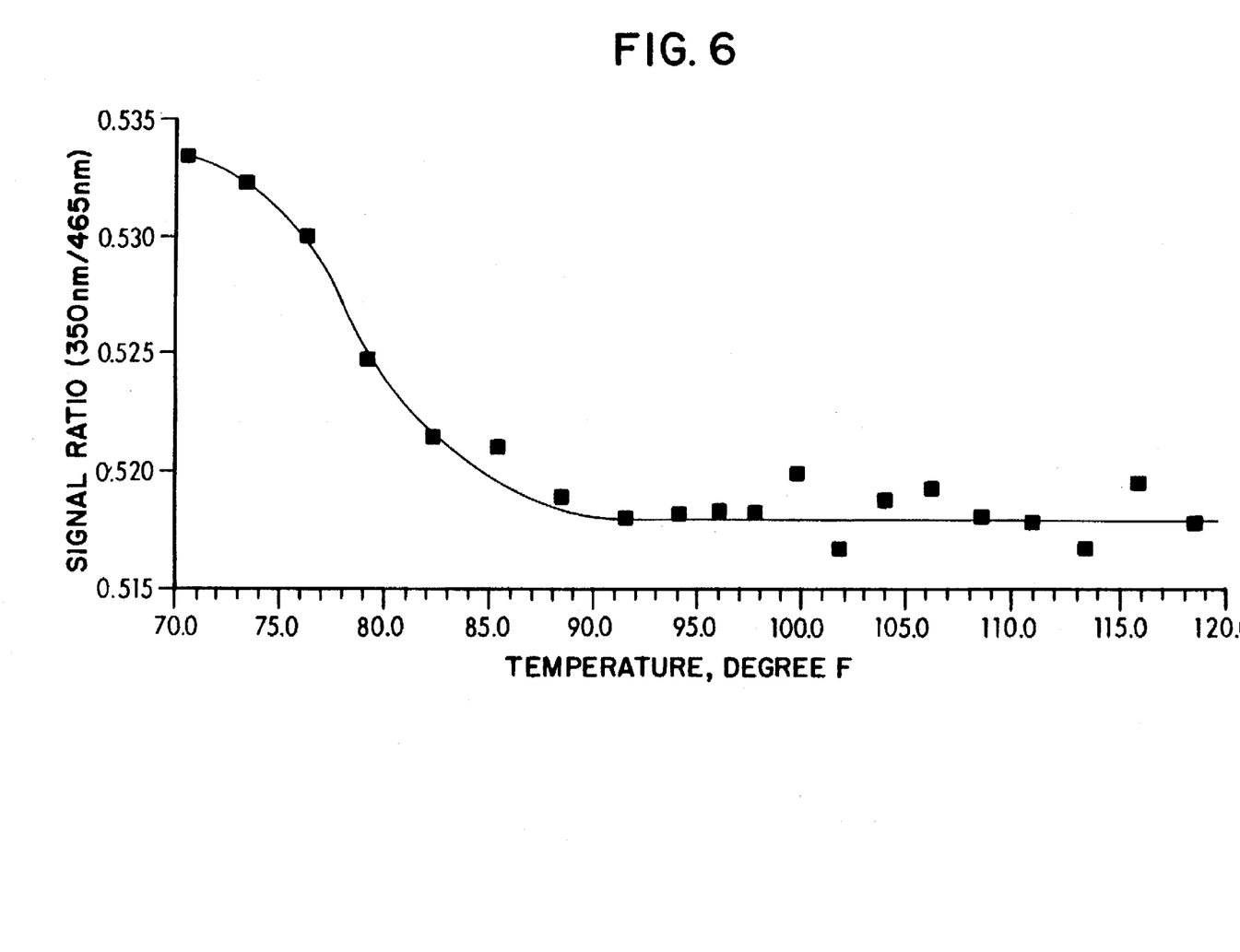
FIG. 6 is a graph showing the ratio of the fluorescence signal intensity at 350 nm to the signal intensity at 465 nm, obtained from a wax-containing crude oil sample, as a function of the sample temperature.

A crude oil bottomhole sample is conditioned overnight in its sample container at 170° F. and 5,000 psig. 100 ml of the conditioned oil is displaced from the hot sample container through a heated line to second volume 57 in cell 50 while maintaining conditions near 170° F. and 5,000 psig. A fiber optic probe is placed in aperture 62 of plug 60, and the cell is rocked while the temperature is decreased linearly from 170° F. to 60° F. at a rate of about 0.3° F./minute while maintaining the pressure at 5,000 psig. An electrical heater and a temperature programmable water bath are used to control the temperature, and a ruska pump and a mineral oil hydraulic fluid are used to drive piston 70 toward plug 60. A Perkin Elmer model LS 50B spectrometer is used to record excitation spectra every 9 minutes with the emission wavelength set at 550 and the excitation wavelength scanned from 300 nm to 500 mm. The ratios of the signals obtained at 350 nm to the signals at 465 nm are plotted in FIG. 6 as a function of sample temperature. The increase in the signal ratio at temperatures lower than 91° F. is due to wax precipitation. The wax cloud point of 91° F. for this sample compares favorably with a value of 95° F. obtained under similar conditions using an infrared scattering technique at a frequency of 2100 $cm^{-1}$.

While the foregoing preferred embodiments of the invention have been described and shown, it is understood that the alternatives and modifications, such as those suggested and others, may be made thereto and fall within the scope of the invention.

We claim:

1. A cell for determining conditions at which organic deposition occurs from a liquid sample, the cell comprising:
    a generally cylindrical housing having a sidewall and first and second opposing ends;
    a first cap secured to said first end of said housing;
    a second cap secured to said second end of said housing;
    means for visually inspecting a liquid sample which is present within said cell;
    means for controlling the temperature of said liquid sample;
    means for controlling the pressure of said liquid sample;
    means for detecting fluorescence changes occurring within the sample; and
    means for measuring an electrical property of the sample, the property selected from the group consisting of conductivity and conductance.

2. The cell of claim 1 wherein said means for controlling the pressure of said liquid sample comprises a piston slidably positioned within the cell.

3. The cell of claim 1 wherein said means for visually inspecting said liquid sample which is present within said cell comprises a transparent window positioned within and secured to said second cap.

4. The cell of claim 3 wherein said transparent window is a sapphire window.

5. The cell of claim 1 wherein said means for detecting fluorescence changes occurring within said sample comprises a fiber optic probe positioned through said second cap.

6. The cell of claim 3 wherein said means for detecting fluorescence changes occurring within said sample comprises a fiber optic probe positioned through said second cap and adjacent said window.

7. The cell of claim 1 wherein said means for measuring said electrical property of the sample comprises two electrodes.

8. The cell of claim 1 wherein said means for controlling the temperature of the liquid sample is a temperature controller electrically connected to a thermocouple positioned on an exterior wall of said cell.

9. The cell of claim 8 wherein said temperature controller is selected from the group consisting of heaters, cooling devices, and combinations thereof.

10. The cell of claim 8 wherein said temperature controller is programmable.

11. A method for determining conditions at which at least one condensed phase forms in an organic liquid sample, the method comprising the steps of:
    controlling the temperature and pressure of a liquid sample;
    detecting changes of one or more physical properties occurring within the sample due to formation of at least one condensed phase in the liquid, the physical properties selected from the group consisting of fluorescence, conductance, conductivity, and combinations thereof; and
    determining the temperature and pressure at which the at least one condensed phase forms.

12. The method of claim 11 wherein changes in fluorescence are detected.

13. The method of claim 12 wherein said fluorescence changes are detected by operating a fluorescence spectrometer in at least one mode selected from the group consisting of emission mode, excitation mode, and synchronous mode.

14. The method of claim 12 further comprising the steps of:
    determining a signature emission fluorescence spectrum for said sample at a first predetermined temperature and a first predetermined pressure;
    selecting at least one emission wavelength from the signature emission fluorescence spectrum;
    obtaining a signature excitation spectrum for said sample at each of the at least one selected emission wavelengths at a second predetermined temperature and a second predetermined pressure; and
    selecting at least two excitation wavelengths from the signature excitation spectrum for detecting said fluorescence changes in said sample while controlling the sample temperature and pressure.

15. The method of claim 14 wherein said first and second predetermined temperatures are the same.

16. The method of claim 14 wherein said first and second predetermined pressures are the same.

17. The method of claim 12 wherein said fluorescence changes result from formation of said at least one condensed phase from said liquid sample.

18. The method of claim 17 wherein said liquid sample is in a container which provides an optical path for detecting said fluorescence changes which result from deposition of said at least one condensed phase on a surface in the optical path.

19. The method of claim 11 wherein said liquid is an oil.

20. The method of claim 19 wherein said at least one condensed phase is a member of the group consisting of asphaltenes, waxes, and combinations thereof.

21. The method of claim 11 wherein changes in an electrical property are detected, the electrical property being conductivity, conductance, or a combination thereof.

22. The method of claim 11 wherein changes in fluorescence and an electrical property are detected simultaneously, the electrical property being conductivity, conductance, or a combination thereof.

23. The method of claim 11 further comprising:

visually inspecting the liquid sample.

24. The method of claim 11 further comprising:

adding a material to said sample prior to detecting said changes in said physical property.

25. The method of claim 24 wherein said material is selected from the group consisting of liquids, gases, and mixtures thereof.

26. The method of claim 11 wherein said temperature is increased to a predetermined value and then decreased at a controlled rate while said changes are detected.

27. The method of claim 11 wherein said at least one condensed phase comprises asphaltenes.

28. The method of claim 11 wherein said at least one condensed phase comprises wax.

* * * * *